United States Patent [19]
Purcell, Jr. et al.

[11] Patent Number: 5,429,635
[45] Date of Patent: Jul. 4, 1995

[54] FIBEROPTIC SPHERICAL DIFFUSER

[75] Inventors: Earl E. Purcell, Jr., Westfield, Mass.; Ronald E. Hille, East Hartland, Conn.

[73] Assignee: Pioneer Optics Company, Windsor Locks, Conn.

[21] Appl. No.: 275,613

[22] Filed: Jul. 13, 1994

[51] Int. Cl.6 .......................................... A61B 17/32
[52] U.S. Cl. .................................... 606/17; 606/15
[58] Field of Search ................................ 606/15, 16, 17

[56] References Cited

U.S. PATENT DOCUMENTS

| | | | |
|---|---|---|---|
| 4,736,743 | 4/1988 | Daikuzono | 606/15 |
| 5,054,867 | 10/1991 | Wagniéres et al. | 385/31 |
| 5,074,632 | 12/1991 | Potter | 385/31 |
| 5,078,711 | 1/1992 | Kakami et al. | 606/16 |

*Primary Examiner*—Stephen C. Pellegrino
*Assistant Examiner*—Sonya C. Harris

[57] ABSTRACT

A fiberoptic diffuser for photodynamic therapy applications comprises an optical fiber having a light transmitting core, cladding about the core, and a buffer layer about the cladding. The distal end portion of the fiber core is free from the cladding and buffer layer, and the exposed distal end of the core has a conical configuration. A cap extends about the distal end portion of the fiber and has a spheroidal end portion of light diffusing material which extends about the exposed conical end of the fiber core. The cap also has a mounting portion engaged with the buffer layer of the fiber, and it provides a cavity in which the exposed core is disposed. Light rays passing through the fiber to its distal end are refracted outwardly at the conical end of the core into the spheroidal end portion of the cap and are further refracted by the cap to exit therefrom over substantially the entire surface of the spheroidal end portion.

16 Claims, 1 Drawing Sheet

FIBEROPTIC SPHERICAL DIFFUSER

BACKGROUND OF THE INVENTION

The present invention relates to fiberoptic devices and, more particularly, to a fiberoptic diffuser providing a generally spherical pattern of light emission.

In a number of medical procedures, it is necessary to deliver a uniform, spherical pattern of light as in the radiation of a spherical organ such as the bladder. One such procedure is photodynamic therapy (PDT), which involves the use of light activated drugs for the treatment of cancers, tumors, or other diseases. The therapy requires that the tissue under treatment be infused with the photoactivatable, medicinal composition, and then the tissue is irradiated with the triggering specific wavelength of light, typically a laser beam delivered by a fiberoptic wave guide.

It is an object of the present invention to provide a novel fiberoptic diffuser which will emit light in a generally spherical pattern.

It is also an object to provide such a fiberoptic diffuser which may be fabricated relatively readily and which is relatively long lived and reliable on operation.

Another object is to provide such a fiberoptic diffuser in which the pattern of light generated therefrom may be varied by varying contours of its components.

SUMMARY OF THE INVENTION

It has now been found that the foregoing and related objects may be readily attained in a fiberoptic diffuser comprising an optical fiber having a light transmitting core, cladding about the core, and a buffer layer about the cladding. The fiber has proximal and distal ends, and the distal end portion of the fiber is free from cladding and buffer to expose the core. The exposed distal end of the core has a conical configuration. Extending about the distal end portion of the fiber is a cap which has a spheroidal end portion of light diffusing material extending about the exposed conical end of the fiber core. The cap also has a mounting portion engaged with the buffer layer of the fiber adjacent the distal end portion, and a cavity in which the exposed core at the distal end portion of the fiber is disposed. As a result, light rays passing through the fiber to its distal end are refracted outwardly at the conical end of the core into the spheroidal end portion of the cap and are further refracted by the cap to exit therefrom over substantially the entire surface of the spheroidal end portion.

Preferably, the conical end of the core has an included angle of about 60°, and the spheroidal configuration of the cap provides a substantially uniform light pattern over an angle of about 300°.

The cavity may be filled with air, or with a substantially transparent material having a low index of refraction.

Desirably, the cap is formed of a transparent material in which is disposed a light scattering component, and a preferred structure is one in which the light scattering component is titanium dioxide particles and the transparent material of the cap is polycarbonate resin.

Conveniently, the mounting portion of the cap is generally tubular, and the mounting portion is internally threaded and threadably engaged upon the fiber.

DETAILED DESCRIPTION OF THE PREFERRED EMBODIMENT

Figure 1:
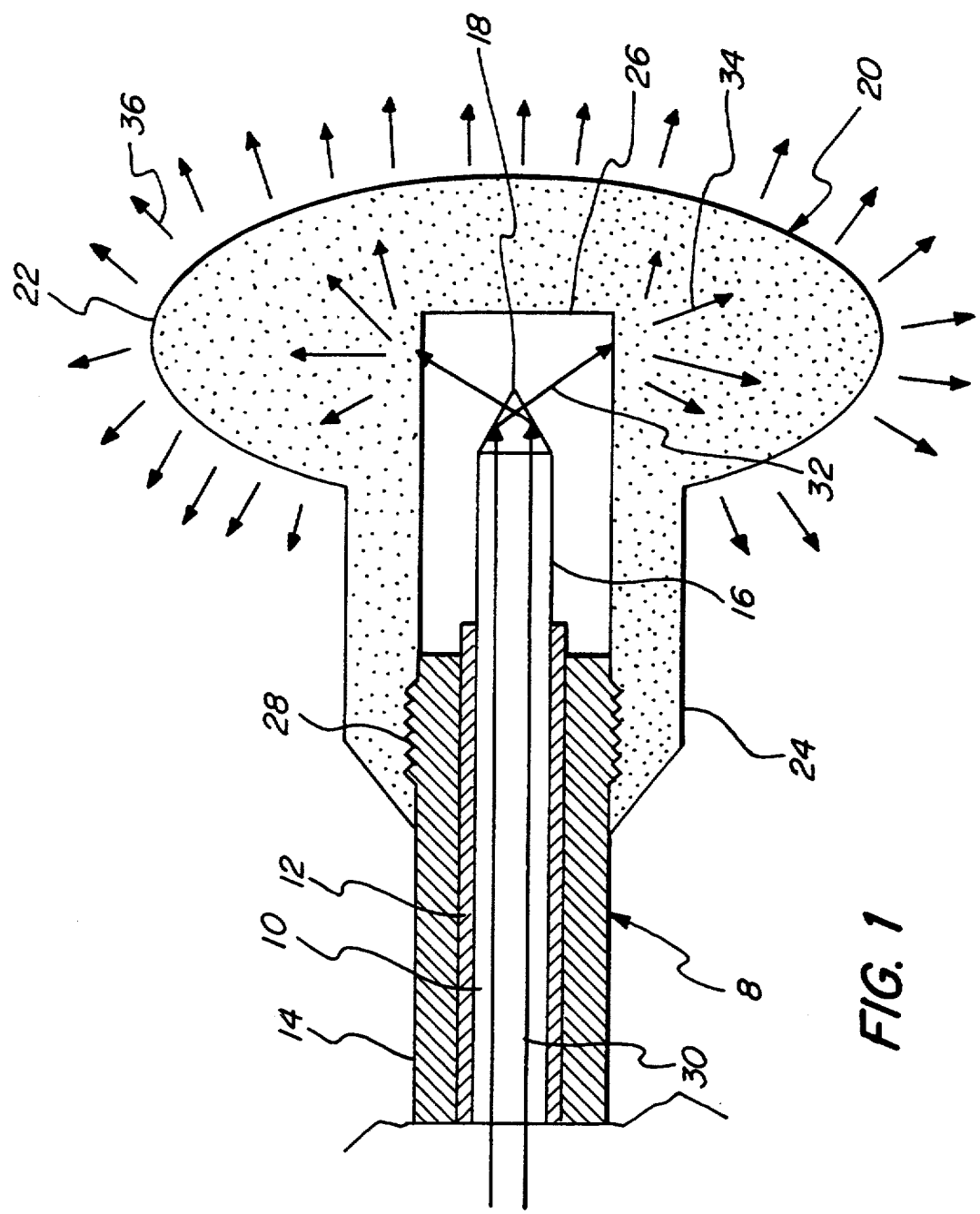
FIG. 1 is a fragmentary sectional view of a fiberoptic diffuser embodying the present invention with arrows indicating the paths of light rays.

As seen in FIG. 1, a fiberoptic diffuser embodying the present invention employs a fiberoptic light guide generally designated by the numeral 8 and having a core 10, cladding 12 extending about the core 10, and an outer buffer layer 14. The distal end portion 16 of the core 10 is free from cladding 12 and buffer layer 14, and it has a generally conical tip 18.

Mounted on the distal end portion 16 of the fiber is a diffuser cap generally designated by the numeral 20 and having a spheroidal portion 22 and a tubular mounting portion 24 of cylindrical cross section. As seen, the outer end of the cavity 26 in the mounting portion 24 is internally threaded as indicated by the numeral 28 to engage the buffer layer 14, and the inner end of the cavity 26 is spaced from the tip 18.

As a result, the light rays indicated by the arrow 30 travelling through the core 10 are reflected at an angle by the conical tip 18 through the cavity 26 into the spheroidal portion 22 of the diffuser cap 20 as illustrated by the arrow 32. As they pass through the spheroidal portion 22 they are refracted in various directions as illustrated by the arrows 34 so as to exit substantially uniformly over substantially the entire surface of the spheroidal portion as illustrated by the arrows 36.

In the preferred embodiment, the distal tip of the fiber core is polished to a cone with a 60° included angle. This angle causes light waves travelling down the fiber to strike the cone at a 30° angle of incidence (well below the critical angle for the silica/air interface) and be totally internally reflected. This ray of light after being reflected off this 30° interface will now strike the opposite side of the cone at a 90° angle of incidence (well above the critical angle) and exit the core 10 at a 60° angle. The function of the cone is to redirect the light energy in the fiber so that it leaves the end of the fiber in a donut of light radiating at an angle of 60°. This change of radiation angle at the core output has two functions:

1. This angle of radiation causes the area where the light first strikes the scattering material to be much larger than if the radiation simply exited the end of the fiber. This larger area means that the power density is lower and therefore the power handling capabilities of the diffuser of this invention are much higher than the current state of the art.

2. By adjusting the position of the donut of light radiation relative to the spheroidal cap of scattering material, the resultant scattered light intensity pattern can be adjusted forwardly (by moving the tip forwardly) or rearwardly (by moving the tip rearwardly). By also modifying the curvature of the spheroid shape of the diffuser cap, the relative scattered light intensity at 90° to the axis of the fiber can be adjusted. A flatter, larger diameter spheroid shape will block light and allow less scattering at a 90° angle to the fiber axis. A longer, smaller diameter spheroidal shape will allow more of the light to be scattered at a 90° angle to the fiber axis.

By adjusting the configuration of the spheroid diffuser cap, the concentration of diffuser material in the cap and the fiber cone tip relative to the spheroidal portion shape, the forward, sideward, and rearward radiation output intensity pattern can be adjusted. In the preferred embodiment illustrated in FIG. 1, a uniform intensity of ±20% over a 300° arc is easily achieved.

Although the preferred included angle for the conical tip is 60°, some variation is permissible depending upon the placement of the tip relative to the center of the spheroidal portion of the cap, and the configuration of the spheroidal portion.

Similarly, although the preferred configuration for the spheroidal portion is that of an ellipsoid, a true spherical configuration may also be employed as can be other spheroidal shapes providing the desired curvilinear surface to ensure radiation over a wide arc.

The spheroidal cap may be fabricated from various materials providing the desired diffusion characteristics. Preferably, the material employed for the matrix of the cap is one which is optically clear, such as a transparent resin and glass, and light scattering particles are uniformly dispersed within this matrix. The preferred resins are polycarbonates although other resins such as epoxies, acrylics, polyvinyl chloride and tetrafluorethylene may also be employed.

The dispersed material is conveniently titanium dioxide pigment particles although other materials such as a lumina, zinc oxide and the like may also be employed.

Although it is possible to mold the cap from the matrix material and dispersed particles, it has been found convenient to machine rod or bar stock into the desired configuration.

In addition to the threaded engagement provided by a thread formed in the cavity of the cap, adhesives may also be employed. Moreover, adhesives may be used as the sole means of attachment as can be crimping.

As a specific example of a fiberoptic diffuser embodying the present invention, an optical fiber supplied by Minnesota Manufacturing and Mining Corporation under the designation FT-400-UMT has it distal end portion stripped by using a fiber buffer strip tool to remove the buffer layer and acetone to remove the cladding. Although only the portion of the core providing the conical tip is required to be free from the cladding and buffer layer, it is desirable to remove the cladding and buffer layer for some distance behind the tip so as to remove these heat sensitive materials from the point of highest output light intensity. The air surrounding the bare core will function as "cladding $\infty$ to preclude any substantial light egress through the unclad portion adjacent the tip.

The tip is conveniently polished into the desired conical configuration by use of a fine polishing paper such as 12 micron grit alumina polishing paper. Other polish angles and polish grit can be used if more or less forward scatter is desired.

The cap is conveniently machined from a 0.125 inch diameter rod of polycarbonate resin containing titanium dioxide colorant and sold by RTP Corporation under the designation Z-21799. The internal thread is conveniently 000-120 standard thread, and a wicking adhesive sold by Loctite Corporation under the name PRIZM 408 is used to firmly lock the cap to the buffer layer of the fiber.

Tests utilizing the fiberoptic diffuser of the present invention establish that the light rays are emitted substantially uniformly over a 300° arc, thus providing the desired wide angle of uniform light emission for irradiation of spherical organs. The configuration and construction of the diffuser allows higher energy inputs by minimizing heat concentration and the assembly is relatively rugged.

Thus, it can be seen that the fiberoptic diffuser of the present invention is one which offers significant advantages for photodynamic therapy and minimizes the risk of over radiation of a small area of the organ being treated. The diffuser may be fabricated readily and relatively economically, and considerable variation in the pattern of radiation can be effected by minor changes in the configuration of the tip and cap.

Having thus described the invention, what is claimed is:

1. A fiberoptic diffuser comprising:
   (a) an optical fiber having a light transmitting core, cladding about said core, and a buffer layer about said cladding, said fiber having proximal and distal ends, a portion of said fiber adjacent said distal end being free from said cladding and said buffer to expose said core, said distal end of said core having a conical configuration; and
   (b) a cap extending about said distal end portion of said fiber and having an end portion of light diffusing material extending about said exposed conical end of said fiber core, said end portion being of spheroidal configuration, said cap also having a mounting portion engaged with said buffer layer of said fiber adjacent said distal end portion and having a cavity in which said exposed core at said distal end portion of said fiber is disposed, said cavity providing a spacing about said distal end portion whereby light rays passing through said fiber to its distal end are reflected outwardly at said conical end of said core into said spheroidal end portion of said cap and are further refracted by said cap to exit therefrom over substantially the entire surface of said spheroidal end portion.

2. The fiberoptic diffuser in accordance with claim 1 wherein said conical end of said core has an included angle of about 60°.

3. The fiberoptic diffuser in accordance with claim 1 wherein said spheroidal configuration of said cap provides a substantially uniform light pattern over an angle of about 300°.

4. The fiberoptic diffuser in accordance with claim 1 wherein said cavity is filled with air.

5. The fiberoptic diffuser in accordance with claim 1 wherein said cavity is filled with a substantially transparent material having a low index of refraction.

6. The fiberoptic diffuser in accordance with claim 1 wherein said cap is formed of a transparent material in which is disposed a light scattering component.

7. The fiberoptic diffuser in accordance with claim 6 wherein said light scattering component is titanium dioxide particles.

8. The fiberoptic diffuser in accordance with claim 6 wherein said transparent material of said cap is polycarbonate resin.

9. The fiberoptic diffuser in accordance with claim 1 wherein said mounting portion of said cap is generally tubular.

10. The fiberoptic diffuser in accordance with claim 9 wherein said mounting cap is internally threaded and threadably engaged upon said fiber.

11. A fiberoptic diffuser comprising:

(a) an optical fiber having a light transmitting core, cladding about said core, and a buffer layer about said cladding, said fiber having proximal and distal ends, a portion of said fiber adjacent said distal end being free from said cladding and said buffer to expose said core, said distal end of said core having a conical configuration; and (b) a cap extending about said distal end portion of said fiber and having an end portion of light diffusing material extending about said exposed conical end of said fiber core, said end portion being of spheroidal configuration, said light diffusing material of said cap being a transparent material in which is disposed a light scattering component, said cap also having a generally tubular mounting portion engaged with said buffer layer of said fiber adjacent said distal end portion and having a cavity in which said exposed core at said distal end portion of said fiber is disposed, said cavity providing a spacing about said distal end portion, whereby light rays passing through said fiber to its distal end are refracted outwardly at said conical end of said core into said spheroidal end portion of said cap and are further refracted by said cap to exit therefrom over substantially the entire surface of said spheroidal end portion.

12. The fiberoptic diffuser in accordance with claim 11 wherein said conical end of said core has an included angle of about 60°.

13. The fiberoptic diffuser in accordance with claim 11 wherein said spheroidal configuration of said cap provides a substantially uniform light pattern over an angle of about 300°.

14. The fiberoptic diffuser in accordance with claim 11 wherein said cavity is filled with air.

15. The fiberoptic diffuser in accordance with claim 11 wherein said light scattering component is titanium dioxide particles and said transparent material of said cap is polycarbonate resin.

16. The fiberoptic diffuser in accordance with claim 11 wherein said mounting portion of said cap is internally threaded and threadably engaged upon said fiber.

* * * * *